United States Patent [19]

Volenec et al.

[11] 4,132,775
[45] Jan. 2, 1979

[54] INFECTIOUS BOVINE RHINOTRACHEITIS VIRUS VACCINE AND METHOD OF PREPARING AND USING THE SAME

[75] Inventors: Frank J. Volenec; Judson D. Todd, both of Overland Park, Kans.

[73] Assignee: Richardson-Merrell Inc., Wilton, Conn.

[21] Appl. No.: 876,998

[22] Filed: Feb. 13, 1978

Related U.S. Application Data

[63] Continuation of Ser. No. 421,438, Dec. 3, 1973, which is a continuation of Ser. No. 94,989, Dec. 3, 1970, abandoned.

[51] Int. Cl.$^2$ .............................................. A61K 39/12
[52] U.S. Cl. ..................................... 424/89; 195/1.3; 424/85; 424/86
[58] Field of Search ........................... 424/89, 85, 86; 195/1.3

[56] References Cited

U.S. PATENT DOCUMENTS 3,366,543   1/1968   Kucera ................................. 196/1.3

Primary Examiner—Shep K. Rose
Attorney, Agent, or Firm—George W. Rauchfuss, Jr.; Eugene O. Retter

[57] ABSTRACT

Pathogenic infectious bovine rhinotracheitis (IBR) virus may be modified by serial passages in non-bovine tissue cultures until it becomes non-pathogenic when applied to the intranasal passages of bovines. Such application will result in the induction of high levels of interferon in nasal secretions as well as the production of local antibodies and a long lasting immunity against IBR infection by virtue of the induction of specific circulating antibodies. The invention includes the method of modifying the IBR virus, a method of preparing a vaccine therefrom and a method of immunizing bovines and promoting production of high levels of interferon in nasal secretions.

5 Claims, No Drawings

INFECTIOUS BOVINE RHINOTRACHEITIS VIRUS VACCINE AND METHOD OF PREPARING AND USING THE SAME

This is a continuation of application Ser. No. 421,438, filed Dec. 3, 1973, which in turn is a continuation of Ser. No. 94,989, filed Dec. 3, 1970 and now abandoned.

This invention relates to a vaccine for the immunization of cattle against infectious bovine rhinotracheitis and for the induction of interferon elaboration in nasal secretions and serum, a method of preparing the vaccine, and a method of immunizing cattle with it.

Infectious bovine rhinotracheitis (IBR) is a highly contagious virus disease of cattle characterized by severe inflammation of the upper respiratory passages and trachea. It is caused by a virus readily transferred by airborne droplets into the respiratory passages of the animals. Infected cattle may have temperatures ranging from 104 to 107° F., a heavy mucous nasal discharge, depression, loss of appetite, increased rate of respiration, labored breathing, and coughing. A secondary bronchial pneumonia occasionally complicates the situation. Another serious sequel to infection is abortion of animals infected during pregnancy. The IBR virus also produces a disease known as infectious pustular vulvovaginitis.

Although the mortality is low, not often in excess of 5%, the morbidity is relatively high and, due to the highly infectious nature of the IBR virus, an entire herd of susceptible cattle may become infected. A serious aspect of the disease is the loss of body weight and condition in feeder cattle due to the depression and loss of appetite, and it becomes necessary to feed these animals for a much longer period of time before they are ready for market. Loss of milk production in a dairy herd is also a serious consequence of the disease.

Several vaccines which are effective in immunizing cattle against IBR are available and a number of patents have issued on methods of preparing these vaccines. For example, U.S. Pat. No. 2,934,473 to York et al. describes a process of modifying the IBR virus by rapid serial passage of the virus in bovine tissue cultures until, it is alleged, the virus is so modified that it will no longer produce disease when injected into normal bovines.

U.S. Pat. No. 2,941,925 to York et al. describes a method of modifying infectious bovine rhinotracheitis virus by propagating it in porcine kidney tissue cultures, resulting in a vaccine which will protect susceptible calves against the disease following parenteral inoculation.

U.S. Pat. No. 3,048,524 to Edmund P. Bass discloses a process of attenuating the IBR virus by serial passage of the virus through canine tissue cultures for at least 10 passages. The vaccine made from this attenuated virus is said to stimulate an antibody response when injected into bovines.

Although the above-mentioned attenuated strains of IBR virus will stimulate the development of protective antibodies in cattle following intramuscular injection, and are effective vaccines in preventing overt disease in cattle exposed to field strains of infectious IBR virus, vaccines made therefrom are not free from disadvantages. For example, it has been found that the vaccine virus may not be sufficiently attenuated so as to be perfectly safe when intramuscularly injected into cattle and is contraindicated for use by the intranasal route because of pathogenic potential. Following intramuscular administration, vaccine virus may appear in respiratory tract secretions of inoculated animals, and this virus may be transferred to the respiratory tract of non-immune cattle which may then develop an infection with the expected clinical signs of the disease. Protection against IBR challenge is expected to appear 10 to 14 days after intramuscular administration of vaccine, such protection being afforded by the development of specific circulating antibodies. The possibility of abortions in pregnant cows is so great that labels on the commercially available vaccine bear a warning to the veterinarian not to inoculate pregnant animals with it. It is evident, therefore, that a more highly attenuated, but safe and effective IBR vaccine should be made available. The present invention accomplishes this purpose.

In brief, the vaccine of the present invention comprises a live IBR virus which has been modified, or attenuated, by serial passage in rabbit kidney tissue cultures to the extent that cattle can be immunized against IBR infection by intranasal vaccination with the virus. The intranasal route is the usual way in which cattle are infected with IBR virus but, as noted above, vaccines currently available cannot be used in this manner because they still retain pathogenic potential. Cattle so inoculated are very apt to develop clinical signs of the disease with all of its serious consequences, including infecting non-immune animals with which they come into contact. The attenuated vaccine of the present invention does not induce clinical signs of the disease but, nevertheless, results in the induction of an IBR antibody titer as high, or usually higher, than when the animals are inoculated intramuscularly with the attenuated IBR virus vaccines currently available.

A number of other important advantages of the present vaccine are also obtained. For example, the risk of abortion by pregnant cows by use of the attenuated vaccine of the present invention is eliminated, or substantially reduced.

The vaccine of the present invention causes the intranasally vaccinated cattle to excrete virus in the nasal secretions for an average of about 11 days, which secretions will immunize non-immune cattle with which the vaccinated animals come in contact. The cattle which have been so infected develop immune antibodies and are resistant to challenge with field strains of pathogenic IBR virus but develop no clinical signs of illness following their contact with intranasally vaccinated cattle. Calves may be allowed to remain with their newly vaccinated dams or with other vaccinated animals and may develop immunity as a result of such contact. This would not be feasible if the animals were vaccinated intramuscularly with one of the less highly attenuated IBR vaccines currently available.

The rabbit kidney attenuated IBR virus of the vaccines of the present invention will not become pathogenic and cause the disease in animals after it has been serially passed in cattle for at least 5 times. However, the vaccine retains its immunizing capacity and calves which were intranasally vaccinated with the virus after 5 serial passages in cattle became infected, without developing clinical signs of the disease, and excreted high titers of virus in their nasal secretions. Calves so vaccinated developed high titers of circulating antibody 10 to 14 days after vaccination.

It has now been recognized that the protective response to viral infection is not limited to the production of antibodies, since these become detectable rather late in the course of the disease. It has been found that there are additional defense mechanisms, operational at the primary sites of infection, which in the case of IBR infection are the nasal passage membranes, which provide more immediate and direct protection than supplied by the antibody that is developed some days after infection. Two mechanisms function at the site of the infection and these are the local antibody system and the interferon mechanism. The secretory antibody includes the IgA class of immunoglobulin and these antibodies are synthesized locally in the respiratory tract. Production of these secretory antibodies is not easily activated by parenteral injection of an antigen, but is readily induced by local administration of the IBR virus. Accordingly, the bovine secretory immune mechanism responds more actively following local antigenic stimulation than by injection of antigen at a distant site.

The release of interferon is one of the earliest demonstrable biological responses to viral infection. Interferon suppresses virus replication. Early development of interferon at the site of infection is therefore important during the period prior to the development of adequate concentrations of protective antibodies throughout the system of the animal. It has been found that intranasal vaccination of cattle with the rabbit tissue culture attenuated virus vaccine of the present invention results in the early development of interferon in the tissues of the respiratory tract of the animal and thus provides preliminary protection against infection. This has been demonstrated by the appearance of high levels of interferon in the nasal secretions of the animals within 40 to 72 hours following vaccination. Lower levels of interferon appear in the serum. Interferon is found in fluids of the respiratory tract until approximately 8 days after vaccination. Intranasal vaccination of bovines results in a detectable titer of IBR neutralizing antibody in their serum by the 10th day and a high titer by the 14th day. Neutralizing antibodies are found in the nasal secretions by the 14th day.

The development of interferon following infection of the nasal tract of bovines with IBR virus is an important advantage of the vaccine of the present invention. On the other hand, calves vaccinated intramuscularly with a bovine kidney attenuated IBR virus vaccine failed to develop detectable amounts of interferon in their nasal secretions and little or no interferon in their serum.

The early development of interferon as occurs when using the vaccine of the present invention is particularly advantageous in protecting calves which are mixed with large numbers of calves entering feed lots from different sources. Not only are the vaccinated calves protected against infection by virulent strains of IBR virus which may be carried by the non-vaccinated calves with which they may come in contact, but they are also protected from other viral infections, inasmuch as interferon protects against viruses of other disease entities. Thus, while the calves vaccinated with the vaccine of the present invention are developing an active immunity against IBR, they are protected from infection by field strains of IBR and are afforded a degree of protection against other viruses as well. Calves which have been inoculated intramuscularly are not so protected. Of course, as noted above, it is a further advantage that the incoming non-vaccinated calves may be immunized by the non-pathogenic IBR virus secreted with the nasal discharges of the vaccinated calves.

Specific details of the preparation of the vaccine of the present invention will now be described. As will be apparent to those skilled in the art, the procedures used are conventional tissue culture techniques and variations in the composition of the culture media, culturing methods, and the like may be made without departing from the essential novelty of the invention. For example, kidney tissues are used as the preferred cells on which the IBR virus is cultured and attenuated, but cells from other organs of these animals may be used. Kidney cells are most convenient, however, for tissue culturing processes, since they seem to grow better than most other cells under in vitro conditions.

The IBR virus that was used in the following procedure was obtained from Dr. Charles York, Veterinary Research Laboratory, Agricultural Experiment Station, Montana State College, Bozeman, Montana, and had been passed through 41 serial passages of bovine kidney cell cultures. When this virus was applied to the nasal passage of calves, these calves developed clinical signs of infectious bovine rhinotracheitis and the virus was not suitable for use as an intranasal vaccine without further modification in accordance with the teachings of the present invention.

As known to those skilled in the art, numerous strains of pathogenic IBR virus which will grow in bovine tissue cultures are readily available and these various strains may be used in practicing the process of the present invention.

Propagation of IBR Virus in Bovine Cells

Cell cultures of bovine embryonic kidney were prepared by standard techniques as follows: Three to six month embryos were obtained from healthy cows, kidneys were removed aseptically, and the kidney cortex and medulla were minced into small segments. These segments were exposed to a solution of 0.25% trypsin in Earle's basic salt solution at a temperature of 37° C. with constant mixing until cells were dispersed. This suspension was centrifuged at 4° C. for 10 minutes at 1000 rpm and the supernatant was discarded. The sedimented cells were resuspended to a final volume concentration of 1:200 in growth medium containing the following ingredients:

| | |
|---|---|
| Earle's Balanced Salt Solution | 80% |
| Lactalbumin hydrolysate, 5% (w/v) aqueous solution | 10% |
| Filtered bovine serum | 10% |
| Polymyxin B | 100 units/ml. |
| Neomycin sulfate | 100 mcg./ml. |
| Amphotericin B | 1 mcg./ml. |

500 milliliters of this suspension of cells were added to each of several Povitsky tissue culture bottles. These bottles were incubated at 37° C. until confluent monolayers of cells covered the bottom surface (4–6 days). Growth medium was then removed and replaced with maintenance medium with the following composition:

| | |
|---|---|
| Earle's Balanced Salt Solution | 88% |
| Lactalbumin hydrolysate, 5% (w/v) aqueous solution | 10% |
| Filtered Bovine Serum | 2% |
| Polymyxin B | 100 units/ml. |
| Neomycin sulfate | 100 mcg./ml. |
| Amphotericin B | 1 mcg./ml. |

Each of these bottles was then inoculated with a 1:80 to 1:500 dilution of the bovine kidney tissue culture propagated York IBR virus (U.S. Pat. No. 2,934,473)

and incubated until 95-100% of the cells were exhibiting changes characteristic of infection (three to five days). Fluids were then harvested, completing the passage. This procedure was repeated 13 times.

Preparation of Rabbit Kidney Cells

Kidneys were removed aseptically from 4 to 6 week old New Zealand White rabbits. The cortex and medulla were minced aseptically into small segments which were placed in a solution containing 0.25% trypsin in Earle's balanced salt solution. This mixture was incubated, with constant agitation, at 37° C. until cells were dispersed. The cell suspension was then centrifuged at 4° C. for 10 minutes at 1000 rpm and the supernatant discarded. The sedimented cells were resuspended at a volume concentration of 1:200 in rabbit kidney (RK) growth medium consisting of the following:

| | |
|---|---|
| Eagle's Minimum Essential Medium* | 80% |
| Lactalbumin hydrolysate, 5% (w/v) aqueous solution | 10% |
| Fetal bovine serum** | 10% |
| Penicillin | 100 units/ml. |
| Streptomycin sulfate | 100 mcg./ml. |
| Amphotericin B | 1 mcg./ml. |

* Literature reference - Eagle, H.: Science 130:432, 1959
** Fetal bovine serum was heat inactivated at 56° C. for 1 hour and sterilized by filtration through a 220 milli-micron membrane filter.

300 milliliters of the cell suspension were added to each of several Povitsky tissue culture bottles which were then incubated at 37° C. until confluent monolayers of cells were formed on the bottom surfaces (5 to 6 days). At this time, the growth medium was removed and replaced with 50 milliliters of a solution consisting of the following:

| Component | mg./Liter |
|---|---|
| NaCl | 8000.0 |
| KCl | 400.0 |
| Dextrose | 1000.0 |
| NaHCO$_3$ | 580.0 |
| Trypsin (1:250) | 500.0 |
| EDTA | 200.0 |

Bottles were incubated for 30 minutes at 37° C. which accomplished the separation of cells from the glass surface and cell dispersion. The cell suspension was centrifuged at 4° C. for 10 minutes at 1000 rpm and the supernatant was discarded. The sedimented cells were resuspended in RK growth medium (as formulated above) at volume concentration of 1:400. 150 ml. of this suspension were added to each of several one liter tissue culture roller bottles which were incubated at 37° C. on a roller drum apparatus providing one revolution every two minutes. Incubation was continued until confluent monolayers of cells were formed (2 to 3 days). At this time, the growth medium was removed and replaced with maintenance medium consisting of Earle's balanced salt solution with 0.5% lactalbumin hydrolysate and 2% fetal bovine serum, supplemented with 100 units penicillin, 100 mcg. streptomycin sulfate and 1 mcg. amphotericin B per milliliter. The virus inoculum was then added at a dilution of 1:100 to the maintenance medium in the roller bottles for infection of the cells.

Inoculation of Rabbit Kidney Cells with IBR Virus

The first roller bottle of RK cells was inoculated with 54th bovine kidney cell culture passage of IBR virus. Volume of the inoculum was 1.0 milliliter containing approximately $\log_{10}$ 6.5 median tissue culture infective particles per milliliter. Virus yield from this inoculum was harvested two days later. Time of harvest was determined, for this passage and for all subsequent passages, by the extent of cytopathic effect (CPE) observed in cells of the RK monolayer. Virus was harvested when from 95 to 100% of the cells had become detached from the glass surface and/or were exhibiting morphologic changes characteristic of advanced infection with IBR virus. These conditions were usually present from 48 to 72 hours following inoculation of virus into roller bottles; therefore, harvests were made 48 to 72 hours after inoculation for all successive passages except passages 19 and 20. These two passages were harvested approximately 30 hours after inoculation. There was no significant difference in virus yields obtained at 30, 48 or 72 hours following inoculation providing the above described criteria for CPE evaluation were present.

Passages one through four (RK-1 through RK-4) were conducted in series, the harvested material from the preceding passage being inoculated directly into a roller bottle of RK cells for the next passage. The volume of inoculum was constant for each passage, being 5.0 milliliters.

Harvested virus material from RK-4 passage was frozen at minus 65 degrees centigrade after having been distributed in 4.0 milliliter volumes into glass vials and tightly stoppered. It was maintained in the frozen state for 60 days, after which time it was thawed and used as inoculum for RK-5. Serial passages from RK-5 to RK-17 were completed as described above for the RK-1 through RK-4 passages. The RK-17 passage virus was frozen as detailed above and maintained for seven weeks, then thawed and inoculated into a roller bottle culture of RK cells for production of RK-18 passage. The RK-18 passage was harvested and was frozen as described above.

Terminal Dilution Cloning

Serial 10-fold dilutions from $\log_{10}$ (−1) through $\log_{10}$ (−8) were prepared from the RK-18 passage virus suspension. One-tenth milliliter of each dilution from $\log_{10}$ (−4) through $\log_{10}$ (−8) was inoculated into each of ten 16 × 150 millimeter glass tissue culture tubes containing monolayers of RK cells prepared as described for culturing of cells in roller bottles except that tubes were incubated in stationary racks at an angle of five degrees from horizontal. Inoculated tubes were incubated at 37 degrees centigrade for six days. After this period of time, one tube, which revealed characteristic cytopathic changes of cells at the highest dilution ($\log_{10}$) (−5) yielding positive tubes, was harvested and the harvested fluid was diluted in serial 10-fold dilutions as described above, each dilution from $\log_{10}$ (−4) through $\log_{10}$ (−8) being inoculated in one-tenth milliliter volumes into each of ten 16 × 150 millimeter tubes containing RK cell monolayers. The first harvest of virus from the one tube (at $10^{-5}$) yielded the Number 1 terminal dilution clone. This was designated RK-19 passage virus. The terminal dilution cloning procedure was conducted in series three times. Number 2 terminal dilution clone virus was harvested after five days of incubation following inoculation and designated RK-20 passage IBR virus. The procedure was repeated, yielding Number 3 terminal dilution clone virus representing RK-21 passage virus.

Production of Vaccine

The RK-21 (Number 3 terminal dilution clone) passage virus was inoculated in a 1.0 ml. volume into a polystyrene tissue culture flask containing a monolayer of RK cells prepared as described above. The bottom surface of the flask measured 75 square centimeters, and the volume of tissue culture maintenance medium was 30 milliliters. The virus yield from this inoculation was harvested after 48 hours incubation at 37° C. and represented RK-22 passage IBR virus.

Ten milliliters of RK-22 passage IBR virus were inoculated into a ten liter roller bottle containing a monolayer of RK cells prepared as described above for the one liter roller bottles except that 1000 milliliters of suspended RK cells were added for outgrowth instead of the 150 milliliters used in the one liter bottles. The virus yield from this inoculation was harvested after 30 hours incubation on the roller drum apparatus at 37° C. This virus represented IBR virus which had undergone 54 passages in bovine kidney cell cultures and 23 passages in rabbit kidney cell cultures. The above product, containing the attenuated virus, constitutes the vaccine of the present invention.

Stabilization of Virus

The virus obtained as described above may be preserved in aliquots of various sizes maintained in sealed glass or polypropylene containers at a temperature of less than minus 40 degrees centigrade, or by freeze drying following the addition of a stabilizing mixture. The stabilizer components and details of the freeze drying (lyophilization) procedure are presented below.

| Stabilizing Preparation Component | Grams/Liter |
|---|---|
| N-Z amine AS | 100.0 |
| Lactose | 100.0 |
| Dextran | 40.0 |
| Monopotassium L-glutamate (monohydrate) | 1.0 |
| Bovine Albumin V | 10.0 |
| Glutathione | 0.4 |
| Distilled water, qs | 1.0 liter |
| One part of stabilizer is mixed with three parts of virus suspension. | |

The virus stabilized bath is then aseptically dispensed via automatic equipment into appropriate sized tubing vials. (For example, tubing vial No. 103- 2 ml. fill, No. 111- 4 ml. fill or No. 118- 8 ml. fill). Lyophilization stoppers are set in each vial and the trays of vials are then frozen to less than $-40°$ C. in the lyophilizer cabinet. When product and cabinet are less than $-40°$ C., the vacuum line between the $-55°$ C. condenser and cabinet is opened allowing lyophilization to proceed. After equilibrium has been established and the vapor pressure in the cabinet is less than $100\mu$, the cabinet temperature is gradually raised in a stepwise fashion not allowing these vapor pressures to exceed $100\mu$. The full cycle is completed when product temperature has remained at 25° C. for 1 hour. The full cycle is approximately 24 hours. Vial stoppers are then set, the vacuum is released and the lyophilized product is removed. Vials are then automatically capped and stored.

Vaccination Procedure

This vaccine is administered by direct instillation of 0.5 to 2.0 milliliters, more or less, of virus suspension containing at least $\log_{10} 4.0$ median tissue culture infective particles into the nostrils of individual bovines. Lower concentrations of the attenuated virus have been shown to induce immunity when applied to the nasal tract of calves, but all calves so vaccinated, for example, with $10^{3.2} TCID_{50}$ concentrations of the virus, did not develop sufficient protective antibodies to resist challenge with virulent field strains of IBR virus. This intranasal instillation may be accomplished by use of a standard medical hypodermic syringe to which is attached a plastic, disposable cannula two inches long with three tiny holes at the terminal end. Alternate methods of inoculation include an aerosol spray directed into the nostrils or by exposure of animals to an aerosol sprayed into a chamber in which animals are held for a period of time to allow inhalation of sufficient amounts of virus into nasal passages.

Treatment with this vaccine should, as a result of demonstrated interferon induction which results in high levels of interferon in nasal secretions and moderate levels in serum, provide protection of variable magnitude against viruses in all major virus groups. Viruses of the arbovirus and myxovirus group classifications are in general most sensitive to the effects of interferon. Bovine viruses which gain access by the respiratory tract should be the ones most effectively inhibited by virtue of the higher levels of interferon present in respiratory tract secretions. Such viruses include, in addition to IBR virus, parainfluenza viruses, rhinoviruses, reoviruses, bovine virus diarrhea virus, bovine adenoviruses, and possibly foot and mouth disease viruses. Such protection would be expected to persist as long as interferon levels are maintained in secretions and serum, which is approximately six to eight days.

The IBR virus attenuated by serial passage in rabbit kidney cell cultures as described above may be mixed with other suitably attenuated viral agents which are safe and effective in vaccinating bovines by the intranasal route, such as, for example, parainfluenza 3, bovine adenoviruses, reoviruses, and other infective viral agents to provide a multivalent vaccine which will, when applied intranasally to the nasal passage membranes of bovines, induce the development of protective antibodies against the several infectious viral agents that have been incorporated in the multivalent vaccine.

Serial passage of virulent IBR virus in bovine tissue cultures is not a critical part of the present invention, and no reason for passing the virus through 50 or more serial passages is known. Serial passage of the virus in bovine tissue cultures adapts the virulent virus to withstand subsequent tissue culturing in rabbit tissue more readily. Also, some virulence is lost during the bovine tissue culturing and it is likely that fewer serial passages in rabbit tissue are subsequently required.

We have found that serial passage of the bovine tissue IBR virus in 18 rabbit kidney tissue cultures is sufficient to attenuate the virus so that it may be safely instilled into the nasal tract of calves without causing them to develop the more serious clinical signs of the disease. It is possible that fewer passages of the virus, for example, 15 serial passages, may be sufficient. On the other hand, continued passage of the virus in rabbit kidney tissue may result in weakening the antigenic properties of the virus so that it is no longer suitable for use in preparing a vaccine. The maximum number of serial passages has, however, not been accurately determined at the present time.

What is claimed is:

1. The non-pathogenic live infectious bovine rhinotracheitis virus vaccine which is effective in protecting bovines against pathogenic strains of infectious bovine rhinotracheitis virus when the bovines are vaccinated by the intranasal route when produced by a method which comprises propagating pathogenic strains of infectious bovine rhinotracheitis virus through at least 41 serial passages of bovine kidney cell cultures followed by at least 23 serial passages in rabbit kidney tissue cultures whereby the pathogenicity of the infectious bovine rhinotracheitis virus is reduced while the ability of the virus to induce the development of protective antibodies is retained.

2. A vaccine of claim 1 wherein the vaccine has been produced by propagating pathogenic strains of infectious bovine rhinotracheitis virus through 54 serial passages of bovine kidney cell cultures followed by 23 serial passages in rabbit kidney tissue cultures.

3. A method of immunizing bovines against infection by pathogenic strains of infectious bovine rhinotracheitis virus which comprises applying to the mucous membranes of the nasal passages of bovines at least $\log_{10} 4.0$ median tissue culture infective particles of a live infectious bovine rhinotracheitis virus of a vaccine prepared according to claim 1.

4. A method of immunizing bovines against infection by pathogenic strains of infectious bovine rhinotracheitis virus which comprises applying to the mucous membranes of the nasal passages of bovines at least $\log_{10} 4.0$ median tissue culture infective particles of a live infectious bovine rhinotracheitis virus of a vaccine prepared according to claim 2.

5. The method of claim 4 wherein the modified virus is applied in the form of an aqueous suspension to each of the nostrils of a bovine.

* * * * *